US012178945B2

(12) United States Patent
Amin et al.

(10) Patent No.: US 12,178,945 B2

(45) Date of Patent: Dec. 31, 2024

(54) CATHETERS, CATHETER-BASED SYSTEMS, AND METHODS THEREOF FOR TREATING HYPERVOLEMIA

(71) Applicant: Bard Peripheral Vascular, Inc., Franklin Lakes, NJ (US)

(72) Inventors: Murtaza Y. Amin, Farmington, UT (US); Nathan Gooch, Centerville, UT (US); Ericka J. Prechtel, Salt Lake City, UT (US); Andrew C. Sheffield, Gilbert, AZ (US); Prabir Roy-Chaudhury, Chapel Hill, NC (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 818 days.

(21) Appl. No.: 17/287,096

(22) PCT Filed: Oct. 24, 2019

(86) PCT No.: PCT/US2019/057874

§ 371 (c)(1),
(2) Date: Apr. 20, 2021

(87) PCT Pub. No.: WO2020/086854

PCT Pub. Date: Apr. 30, 2020

(65) Prior Publication Data

US 2021/0386919 A1 Dec. 16, 2021

Related U.S. Application Data

(60) Provisional application No. 62/750,124, filed on Oct. 24, 2018.

(51) Int. Cl.

*A61M 1/34* (2006.01)
*A61M 1/00* (2006.01)
*A61M 1/16* (2006.01)

(52) U.S. Cl.

CPC ........ *A61M 1/1678* (2013.01); *A61M 1/3403* (2014.02); *A61M 1/3482* (2014.02); *A61M 1/60* (2021.05)

(58) Field of Classification Search

CPC ...... A61M 1/159; A61M 1/1678; A61M 1/34; A61M 1/3403; A61M 1/3482; A61M 1/60;

(Continued)

(56) References Cited

U.S. PATENT DOCUMENTS 3,701,433 A * 10/1972 Krakauer ............... B01D 36/02
D24/162
4,657,530 A 4/1987 Buchwald et al.

(Continued)

FOREIGN PATENT DOCUMENTS

EP 1393770 A1 3/2004
WO 13122580 A1 8/2013

(Continued)

OTHER PUBLICATIONS

PCT/US2019/057874 filed Oct. 24, 2019 International Search Report and Written Opinion dated Feb. 14, 2020.

*Primary Examiner* — Leslie A Lopez
*Assistant Examiner* — Jihad Dakkak
(74) *Attorney, Agent, or Firm* — Rutan & Tucker LLP

(57) ABSTRACT

A catheter (100) for treating hypervolemia in a patient includes a luminal ingress (112) joined to a luminal egress (114) at a distal end portion (116) of the catheter having a closed distal end (102). The distal end portion is configured to at least temporarily reside within a vessel of the patient, the distal end portion including a semipermeable membrane. The luminal ingress is designed to convey an influent having a first osmotic concentration to the distal end portion. The semipermeable membrane is configured to pass blood-borne (Continued)

water from the vessel into the distal portion. The blood-borne water is absorbed by the influent to produce an effluent having a second osmotic concentration lower than the first osmotic concentration. Systems (200) with the catheter and methods for treating hypervolemia are also disclosed.

23 Claims, 2 Drawing Sheets

(58) Field of Classification Search
CPC .. A61M 2025/0004; A61M 2025/0039; A61M 2025/004; A61M 2025/006; A61M 2039/0036; A61M 2039/0211; A61M 2039/0214; A61M 2039/0241; A61M 2039/1072; A61M 2202/0042; A61M 2202/0413; A61M 2202/0415; A61M 25/0021; A61M 25/0067; A61M 25/0082; A61M 27/002; A61M 39/0208
See application file for complete search history.

(56) References Cited

U.S. PATENT DOCUMENTS 4,725,207 A 2/1988 Buchwald et al.
5,037,385 A 8/1991 O'Byrne
5,092,886 A * 3/1992 Dobos-Hardy ..... A61M 1/3496 623/23.65
5,397,354 A * 3/1995 Wilk ...................... A61F 2/022 623/23.65
5,545,131 A * 8/1996 Davankov ........... A61M 1/3679 210/646
5,735,809 A * 4/1998 Gorsuch ............. B01D 63/024 604/6.04
5,902,336 A 5/1999 Mishkin
8,211,053 B2 7/2012 Herbert
8,641,659 B2 2/2014 Soykan et al.
8,876,850 B1 11/2014 Vollmers et al.
9,039,646 B2 5/2015 Lande
9,138,523 B2 9/2015 Burnett et al.
9,295,764 B2 3/2016 Christensen et al.
9,393,387 B1 7/2016 Mayse et al.
9,656,049 B1 5/2017 Khan et al.
9,675,327 B2 6/2017 Johnson et al.
9,913,968 B2 3/2018 Burnett
9,919,138 B2 3/2018 Lenihan et al.
9,956,336 B2 5/2018 Degen et al.
2002/0115956 A1* 8/2002 Ross .................. A61M 1/3403 604/6.04
2009/0234266 A1 9/2009 Solomon et al.
2010/0312163 A1 12/2010 Forsell
2014/0012180 A1 1/2014 Levin et al.
2015/0343186 A1 12/2015 Nitzan et al.
2016/0030658 A1* 2/2016 van der Merwe .......................... A61M 1/362265 604/67
2017/0128654 A1 5/2017 Feld
2018/0056050 A1 3/2018 Degen et al.
2018/0060520 A1 3/2018 Degen et al.
2018/0229015 A1 8/2018 Pisano et al.
2018/0344917 A1 12/2018 Inhaber et al.

FOREIGN PATENT DOCUMENTS

WO 18211500 A1 11/2018
WO 18224351 A1 12/2018

* cited by examiner

CATHETERS, CATHETER-BASED SYSTEMS, AND METHODS THEREOF FOR TREATING HYPERVOLEMIA

PRIORITY

This application is a U.S. national stage application from International Application No. PCT/US2019/057874, filed Oct. 24, 2019, which claims the benefit of priority to U.S. Provisional Patent Application No. 62/750,124, filed Oct. 24, 2018, each of which is incorporated by reference in its entirety into this application.

BACKGROUND

Hypervolemia, or fluid overload, is a medical condition in which the volume of blood in the intravascular compartment is in excess of normal as a result of plasma retaining too much water. Water can accumulate in patients suffering from chronic kidney disease, particularly in advanced stages thereof such as end-stage renal disease ("ESRD"), where the kidneys are no longer effective in filtering out water in excess of that the body needs. Water can also accumulate in patients suffering from chronic heart disease such as congestive heart failure ("CHF"), where the heart is no longer effective in pumping the blood to the kidneys to filter out the water in excess of that the body needs. The volume of blood in the intravascular compartment in excess of normal can lead to hypertension, stress on the heart, and cause shortness of breath due to fluid buildup in the pleural cavity, which can degrade quality of life and even exacerbate other diseases such as CHF leading to death. Therefore, managing hypervolemia is important to those suffering from the medical condition. Disclosed herein are catheters, catheter-based systems, and methods thereof that address the foregoing.

SUMMARY

Disclosed herein is a catheter for treating hypervolemia in a patient including, in some embodiments, a luminal ingress joined to a luminal egress at a distal end portion of the catheter having a closed distal end. The distal end portion is configured to at least temporarily reside within a vessel of the patient, the distal end portion including a semipermeable membrane. The luminal ingress is designed to convey an influent having a first osmotic concentration to the distal end portion. The semipermeable membrane is configured to pass blood-borne water from the vessel into the distal portion. The blood-borne water is absorbed by the influent to produce an effluent having a second osmotic concentration lower than the first osmotic concentration.

In some embodiments, the catheter is a single-lumen catheter. The single lumen is folded at a fold proximal of the closed end of the catheter.

In some embodiments, the catheter further includes a septum disposed between the luminal ingress and the luminal egress. A distal end of the septum is proximal of the closed end of the catheter.

In some embodiments, the semipermeable membrane has a pore size configured to allow the water in the patient's vessel to permeate through the semipermeable membrane but not larger blood-borne metabolites including polypeptides or proteins, cell fragments, or cells.

In some embodiments, an abluminal surface of the catheter includes a surface area-increasing means to increase a surface area of the abluminal surface over such a catheter without the surface area-increasing means. The surface area-increasing means increases a flux of the water from the patient's vessel through the semipermeable membrane.

In some embodiments, the influent is an aqueous solution including a dissolved polymer. The first osmotic concentration is sufficient to create an osmotic potential for removing the water from the vessel in excess of that the patient needs through the semipermeable membrane.

Also disclosed herein is a catheter for treating hypervolemia including, in some embodiments, a folded lumen of the catheter including a luminal ingress and a luminal egress joined at a 'U'-shaped distal end portion of the folded lumen proximate a closed end of the catheter. A distal end portion of the catheter including the closed end of the catheter is configured to at least temporarily reside within a vessel of a patient's intravascular compartment. At least the distal end portion of the catheter configured to reside within the patient's vessel is formed of a semipermeable membrane. The semipermeable membrane is configured to allow blood-borne water in the patient's vessel to permeate through the semipermeable membrane into an influent having a first osmotic concentration conveyed by the luminal ingress to produce an effluent having a second osmotic concentration conveyed by the luminal egress, wherein the second osmotic concentration is lower than the first osmotic concentration.

In some embodiments, the catheter further includes a septum disposed between the luminal ingress and the luminal egress. A distal end of the septum is short of the closed end of the catheter, thereby forming the 'U'-shaped distal end portion of the folded lumen proximate the closed end of the catheter.

In some embodiments, the semipermeable membrane has a pore size configured to allow the water in the patient's vessel to permeate through the semipermeable membrane but not larger blood-borne metabolites including polypeptides or proteins, cell fragments, or cells.

In some embodiments, an abluminal surface of the catheter includes a surface area-increasing means to increase a surface area of the abluminal surface over such a catheter without the surface are-increasing means. The surface-area-increasing means increases a flux of the water from the patient's vessel through the semipermeable membrane.

Also disclosed herein is a system for treating hypervolemia in a patient including, in some embodiments, a catheter and fluid-collection system. The catheter includes a luminal ingress joined to a luminal egress at a distal end portion of the catheter having a closed distal end. The distal end portion is configured to at least temporarily reside within a vessel of the patient, the distal end portion including a semipermeable membrane. The luminal ingress is designed to convey an influent having a first osmotic concentration to the distal end portion. The semipermeable membrane is configured to pass blood-borne water from the vessel into the distal portion. The blood-borne water is absorbed by the influent to produce an effluent having a second osmotic concentration lower than the first osmotic concentration. The fluid-collection system includes a reservoir configured to collect the effluent and a pump configured to move one or more fluids of the system including the influent and the effluent.

In some embodiments, the fluid-collection system further includes an ultrafiltration membrane configured to produce a membrane permeate consisting essentially of the water from the patient's vessel and a membrane retentate for the influent.

In some embodiments, the fluid-collection system further includes a shunt configured to shunt the membrane permeate to a bladder of the patient for elimination.

In some embodiments, the fluid-collection system further includes a switch valve configured to switch a mode of the fluid-collection system from collecting the water from the patient's vessel in the reservoir to producing the membrane permeate and the membrane retentate for influent.

In some embodiments, the catheter further includes a septum disposed between the luminal ingress and the luminal egress, wherein a distal end of the septum is proximal of the closed end of the catheter.

In some embodiments, the semipermeable membrane has a pore size configured to allow the water in the patient's vessel to permeate through the semipermeable membrane but not larger blood-borne metabolites including polypeptides or proteins, cell fragments, or cells.

In some embodiments, the influent is an aqueous solution including a dissolved polymer. The first osmotic concentration is sufficient to create an osmotic potential for removing the water from the vessel in excess of that the patient needs through the semipermeable membrane.

Also disclosed herein is a system for treating hypervolemia including, in some embodiments, a catheter and a fluid-collection system. The catheter includes a folded lumen including a luminal ingress and a luminal egress joined at a 'U'-shaped distal end portion of the folded lumen proximate a closed end of the catheter. A distal end portion of the catheter including the closed end of the catheter is configured to at least temporarily reside within a vessel of a patient's intravascular compartment. At least the distal end portion of the catheter configured to reside within the patient's vessel is formed of a semipermeable membrane. The semipermeable membrane is configured to allow blood-borne water in the patient's vessel to permeate through the semipermeable membrane into an influent having a first osmotic concentration conveyed by the luminal ingress to produce an effluent having a second osmotic concentration conveyed by the luminal egress, wherein the second osmotic concentration is lower than the first osmotic concentration. The fluid-collection system includes a reservoir configured to collect the effluent and a pump configured to move one or more fluids of the system including the influent and the effluent.

In some embodiments, the fluid-collection system further includes an ultrafiltration membrane configured to produce a membrane permeate consisting essentially of the water from the patient's vessel and a membrane retentate for the influent.

In some embodiments, the fluid-collection system further includes a shunt configured to shunt the membrane permeate to a bladder of the patient for elimination.

In some embodiments, the fluid-collection system further includes a switch valve configured to switch a mode of the fluid-collection system from collecting the water from the patient's vessel in the reservoir to producing the membrane permeate and the membrane retentate.

In some embodiments, the catheter further includes a septum disposed between the luminal ingress and the luminal egress. A distal end of the septum is short of the closed end of the catheter, thereby forming the 'U'-shaped distal end portion of the folded lumen proximate the closed end of the catheter.

In some embodiments, the semipermeable membrane has a pore size configured to allow the water in the patient's vessel to permeate through the semipermeable membrane but not larger blood-borne metabolites including polypeptides or proteins, cell fragments, or cells.

Also disclosed herein is a method for treating hypervolemia including, in some embodiments, inserting a closed-ended catheter in a vessel of a patient. The catheter includes a distal end portion having a semipermeable membrane and a luminal ingress joined to a luminal egress at the distal end portion. The method further includes directing an influent into the luminal ingress having a first osmotic concentration; absorbing blood-borne water from the vessel into the distal end portion through the semipermeable membrane to produce an effluent having a second osmotic concentration lower than the first osmotic concentration; and directing the effluent out of the catheter by way of the luminal egress.

In some embodiments, the method further includes pumping the influent into the luminal ingress and pumping the effluent out of the luminal egress with a pump fluidly coupled to the catheter.

In some embodiments, the method further includes disposing the effluent as a waste product.

In some embodiments, the method further includes recycling the effluent with a fluid-collection system to produce the influent.

In some embodiments, directing the effluent out of the catheter includes directing the effluent into a fluid reservoir of the fluid-collection system.

In some embodiments, the method further includes switching a mode of the fluid-collection system from collecting the effluent with the fluid reservoir to filtering the effluent with an ultrafiltration membrane of the fluid-collection system. Filtering the effluent produces a water-based membrane permeate and a membrane retentate of the influent.

In some embodiments, the method further includes shunting the membrane permeate to a bladder of the patient for elimination.

These and other features of the concepts provided herein will become more apparent to those of skill in the art in view of the accompanying drawings and following description, which disclose particular embodiments of such concepts in greater detail.

DRAWINGS

DESCRIPTION

Figure 1:
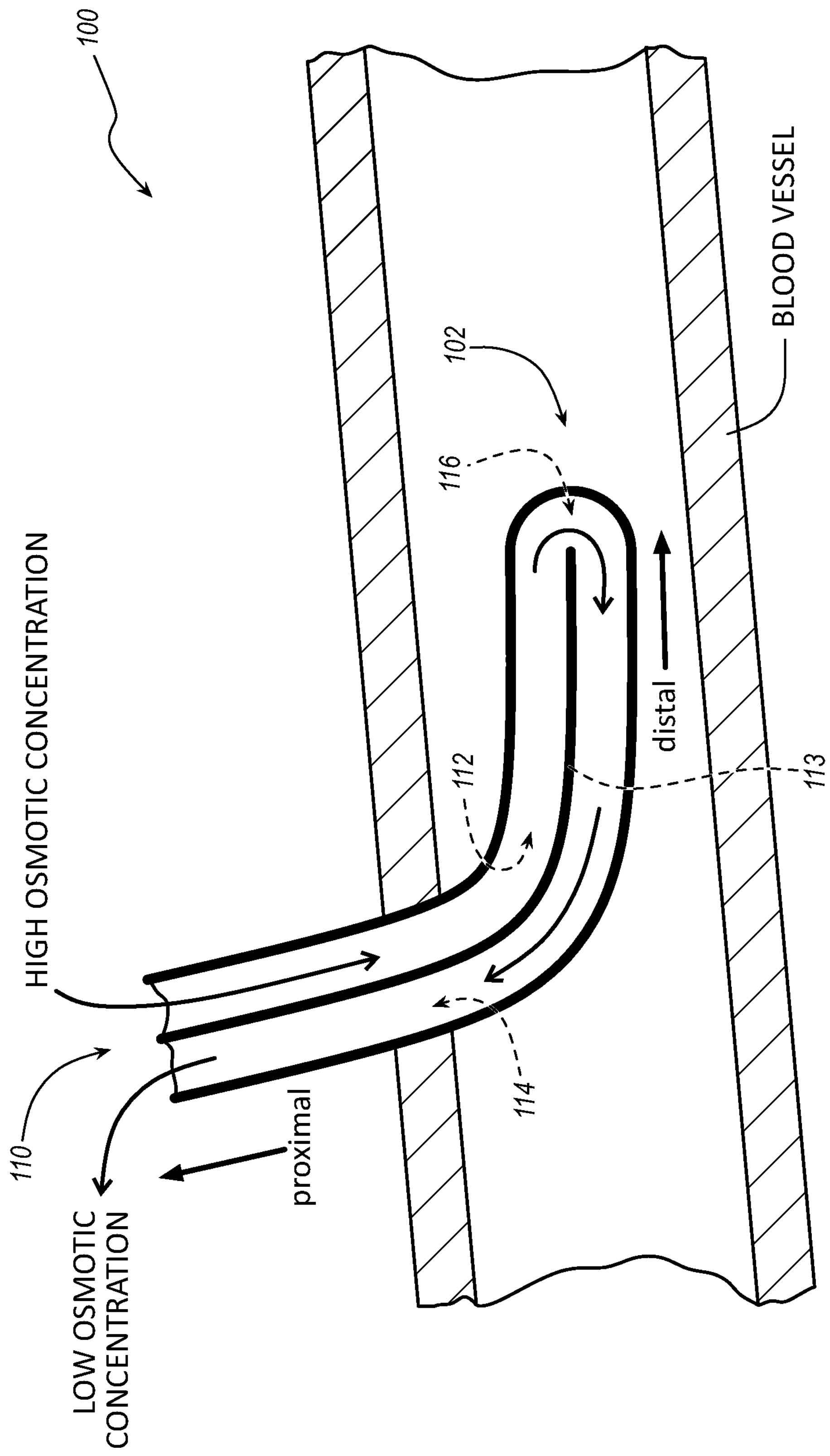
FIG. 1 illustrates a catheter for treating hypervolemia in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, hypervolemia is a medical condition in which the volume of blood in the intravascular compartment is in excess of normal as a result of plasma retaining too much water. Water can accumulate in patients suffering from chronic kidney disease, particularly in advanced stages thereof such as ESRD, where the kidneys are no longer effective in filtering out water in excess of that the body needs. Water can also accumulate in patients suffering from chronic heart disease such as CHF, where the heart is no longer effective in pumping the blood to the kidneys to filter out the water in excess of that the body needs. The volume of blood in the intravascular compartment in excess of normal can lead to hypertension, stress on the heart, and cause shortness of breath due to fluid buildup in the pleural cavity, which can degrade quality of life and even exacerbate other diseases such as CHF leading to death. Therefore, managing hypervolemia is important to those suffering from the medical condition. Disclosed herein are catheters, catheter-based systems, and methods thereof that address the foregoing.

Catheters

FIG. 1 illustrates a catheter 100 for treating hypervolemia in accordance with some embodiments.

As shown, the catheter 100 for treating hypervolemia includes a folded lumen 110 of the catheter 100 including a luminal ingress 112 and a luminal egress 114 joined at a 'U'-shaped distal end portion 116 of the folded lumen 110 proximate a closed end 102 of the catheter 100. A distal end portion of the catheter 100 including the closed distal end of the catheter 100 is configured to at least temporarily reside within a vessel of a patient's intravascular compartment. At least the distal end portion of the catheter 100 configured to reside within the patient's vessel is formed of a semipermeable membrane. The semipermeable membrane is configured to allow blood-borne water in the patient's vessel to permeate through the semipermeable membrane into an influent having a first osmotic concentration conveyed by the luminal ingress 112 to produce an effluent having a second osmotic concentration conveyed by the luminal egress 114, wherein the second osmotic concentration is lower than the first osmotic concentration.

The catheter 100 further includes a septum 113 disposed between the luminal ingress 112 and the luminal egress 114, thereby forming the luminal ingress 112 and the luminal egress 114. A distal end of the septum 113 is proximate the closed end of the catheter 100. Indeed, distal end of the septum 113 is just short of the closed end 102 of the catheter 100, thereby forming the 'U'-shaped distal end portion 116 of the folded lumen 110 proximate the closed end 102 of the catheter 100. As such, the catheter 100 is a single-lumen catheter folded at a fold proximal of the closed end of the catheter. That said, multi-lumen catheters using the concepts provided herein are also possible.

The semipermeable membrane of the catheter 100 has pores of a pore size that allow the water in the patient's vessel to permeate through the semipermeable membrane but not larger blood-borne metabolites such as polypeptides or proteins, cell fragments such as platelets, or cells such as red blood cells or white blood cells. However, the pores of the semipermeable membrane can be sized to allow ions such as $Na^+$, $K^+$, $Ca^{2+}$, $Mg^{2+}$, or $Cl^-$ to permeate through the semipermeable membrane, as well as molecules of lower molecular weight than the foregoing larger metabolites such as urea or creatinine. An example of such a membrane includes, but is not limited to, a dialysis membrane.

An abluminal surface, or outer surface, of the catheter 100 can include a surface area-increasing means to increase a surface area of the abluminal surface beyond that of a flat, smooth abluminal surface. The surface area-increasing means includes, but is not limited to, convolutions, corrugations, fins, or a combination thereof. The surface-area-increasing means increases a flux of the water from the patient's vessel through the semipermeable membrane.

As shown, the influent is conveyed by the luminal ingress 112 to the 'U'-shaped distal end portion 116 of the folded lumen 110 where, along the way, the influent draws the water from the patient's vessel through the semipermeable membrane into the influent by way of osmosis. The influent can be sourced from a periodically refreshed influent reservoir such as by pumping the influent from the influent reservoir into the luminal ingress 112 with a pump. The influent, which has a first or initial osmotic concentration, ultimately becomes the effluent having a second or final osmotic concentration less than the initial osmotic concentration upon absorbing the water from the patient's vessel. The influent transitions into the effluent along both the 'U'-shaped distal end portion 116 and the luminal egress 114 of the folded lumen 110 as long as there is an osmotic potential to do so. The effluent can be conveyed by the luminal egress 114 to an effluent reservoir for disposal using the same action of pumping the influent from the influent reservoir into the luminal ingress 112 with the pump.

The influent can be an aqueous solution including a dissolved polymer such as poly(ethylene glycol) ("PEG") or sodium polyacrylate in a concentration sufficient to create the osmotic potential for removing the water from the patient's vessel in excess of that the patient needs through the semipermeable membrane during a treatment session therefor.

The catheter 100 can be configured as a long-term implant, or the catheter 100 can be configured to be swapped out periodically. With respect to the latter, the catheter 100 can be disposable in that the catheter 100 can be implanted into a patient's arteriovenous fistula at the end of each dialysis session for use between dialysis sessions, such as overnight when the patient is asleep. The influent used with the catheter 100, or the effluent produced therefrom, (i.e., the fluid used with the catheter 100) can be disposable as well. The influent can be supplied in a ready-to-use cartridge along with an empty cartridge for disposal of the effluent. An external pump can be used to pump the influent from an influent cartridge to an effluent cartridge through the catheter 100, during which the influent becomes the effluent as described herein. The pump can be powered by batteries or mains electricity.

In view of the foregoing, the catheter 100 is configured to remove the water in excess of that the patient's needs from the patient's bloodstream. Thus, the catheter 100 can improve the patient's quality of life by reducing hypervolemia, thereby reducing the amount of water that needs to be removed at each dialysis session, as well as the number of dialysis sessions required by the patient per week.

Catheter System

Figure 2:
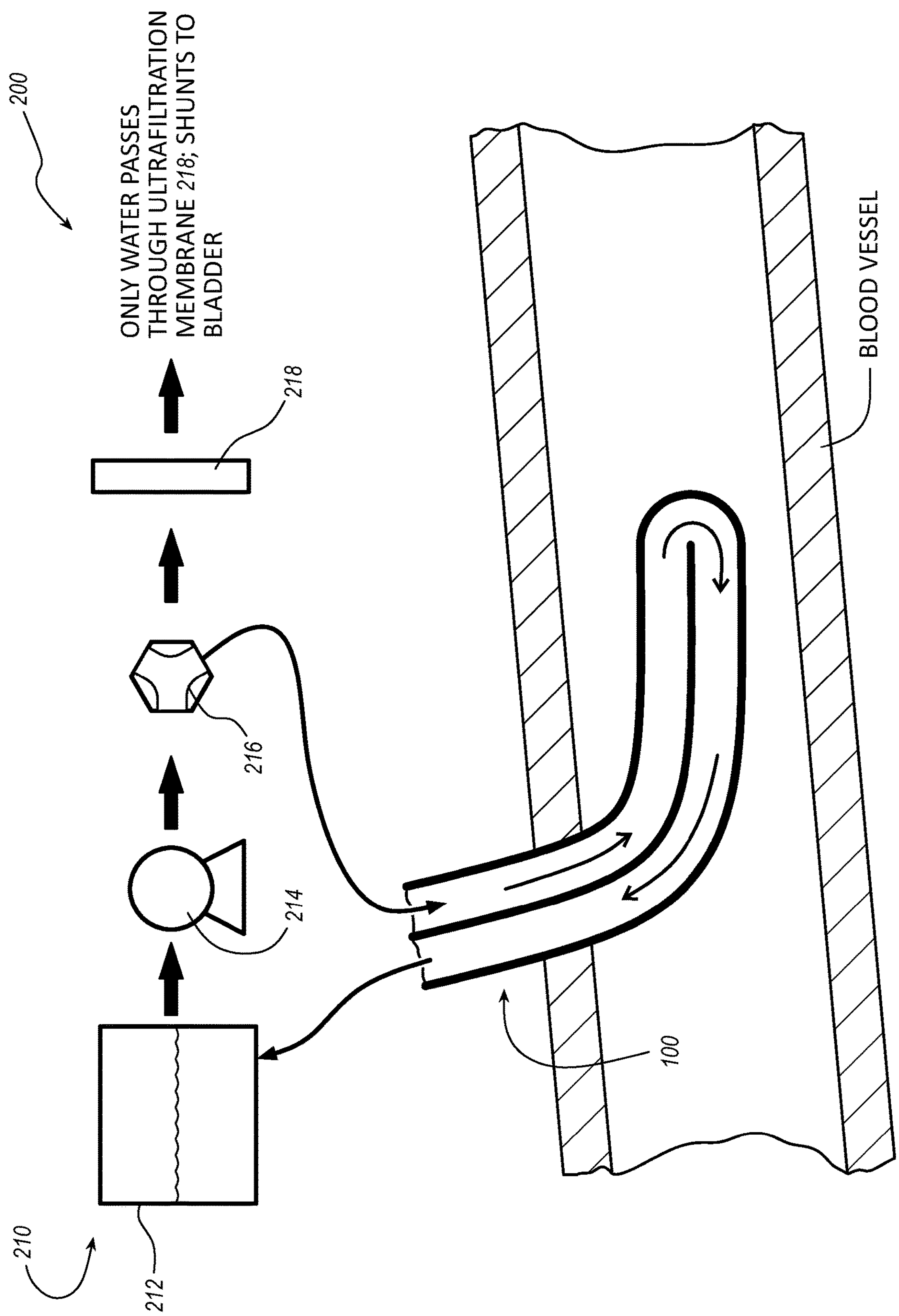
FIG. 2 illustrates a system for treating hypervolemia in accordance with some embodiments.

FIG. 2 illustrates a system 200 for treating hypervolemia in accordance with some embodiments.

Also disclosed herein is a system 200 for treating hypervolemia including, in some embodiments, the catheter 100 described herein above and a fluid-collection system 210. The fluid-collection system 210 includes a fluid reservoir 212 configured to collect the effluent, and a pump 214 configured to move one or more fluids of the system 210 including the influent and the effluent.

The fluid-collection system 210 can further include an ultrafiltration membrane 218 configured to produce a membrane permeate consisting essentially of the water from the patient's vessel. The ultrafiltration membrane 218 increases an osmotic concentration of a membrane feed to the ultrafiltration membrane 218, which membrane feed becomes membrane retentate in the fluid reservoir 212 for the influent.

Ultrafiltration such as with the ultrafiltration membrane 218 requires the pump 214 be able to produce relatively high pressures for the ultrafiltration, which, in turn, requires the pump 214 to be powered from outside the system 200. Such power can be supplied by mains electricity, optionally through an inductive coupling beneath the patient's skin. The power can be applied at night to allow the system 200 to recharge.

The fluid-collection system 210 can further include a shunt configured to shunt the membrane permeate to a bladder of the patient for elimination. When the fluid-collection system 210 is configured with the shunt, the catheter 100 of the system 200 can be configured for long-term implantation such as in a renal vein of the patient in order to have immediate access to a ureter in which to shunt the membrane permeate for elimination through the bladder of the patient.

The fluid-collection system 210 further includes a switch valve 216 configured to switch a mode of the fluid-collection system 210 from collecting the water from the patient's vessel in the fluid reservoir 212 to producing the membrane permeate and the membrane retentate. Instead of the disposable fluid used with the disposable embodiment of the catheter 100 described herein above, the fluid used with the instant embodiment of the catheter 100 is reusable by way of removing the water absorbed from the patient with the ultrafiltration membrane 218. Indeed, when the fluid reservoir 212 achieves a certain volume of effluent therein, or reaches a certain pressure exerted by the effluent, the switch valve 216 can be actuated to switch the mode of the fluid-collection system 210 from collecting the water from the patient's vessel in the fluid reservoir 212 by way of pumping fluid through the catheter 100 to producing the membrane permeate and the membrane retentate.

In addition to the benefits of the disposable embodiment of the catheter 100 described herein above, long-term implantation of the catheter 100 might reduce risk of infection and lessen restriction on the patient's day-to-day life compared to the disposable embodiment of the catheter 100.

Methods

A method for treating hypervolemia including, in some embodiments, inserting a closed-ended catheter such as the catheter 100 in a vessel of a patient. As described herein above, the catheter 100 includes the distal end portion having the semipermeable membrane and the luminal ingress 112 joined to the luminal egress 114 at the distal end portion. The method further includes directing the influent described herein above into the luminal ingress 112 having the first osmotic concentration; absorbing blood-borne water from the vessel into the distal end portion through the semipermeable membrane to produce an effluent having a second osmotic concentration lower than the first osmotic concentration; and directing the effluent out of the catheter 100 by way of the luminal egress 114.

The method further includes pumping the influent into the luminal ingress 112 and pumping the effluent out of the luminal egress 114 with the pump described herein above when the pump is fluidly coupled to the catheter 100.

The method further includes disposing the effluent as a waste product as described in reference to the disposable embodiment of the catheter 100 described herein above. For example, the effluent can be pumped into the empty cartridge for the effluent, and the cartridge including the effluent can be disposed as the waste product.

The method further includes recycling the effluent with the fluid-collection system 210 to produce the influent. When the fluid-collection system 210 is used, directing the effluent out of the catheter 100 includes directing the effluent into the fluid reservoir 212 of the fluid-collection system 210. At a time when the fluid reservoir 212 achieves a certain volume of effluent therein, or reaches a certain pressure exerted by the effluent, the mode of the fluid-collection system 210 is switched from collecting the effluent with the fluid reservoir 212 to filtering the effluent with the ultrafiltration membrane 218 of the fluid-collection system 210. Filtering the effluent produces a water-based membrane permeate and a membrane retentate of the influent. The membrane permeate can then be shunted to a bladder of the patient for elimination.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter for treating hypervolemia in a patient, comprising:

a distal end portion having a closed distal end configured to at least temporarily reside within a vessel of the patient;

a luminal ingress joined to a luminal egress at the distal end portion, the luminal ingress designed to convey an influent having a first osmotic concentration to the distal end portion, wherein an abluminal surface of the luminal ingress is configured to be in direct contact with a fluid within the vessel of the patient; and a semipermeable membrane configured to pass blood-borne water from the vessel into at least the distal end portion, the blood-borne water absorbed by the influent to produce an effluent having a second osmotic concentration lower than the first osmotic concentration.

2. The catheter according to claim 1, wherein the catheter is a single-lumen catheter, the single-lumen catheter folded at a fold proximal of the closed end of the catheter.

3. The catheter according to claim 1, further comprising a septum disposed between the luminal ingress and the luminal egress, wherein a distal end of the septum is proximal of the closed distal end of the catheter.

4. The catheter according to claim 1, wherein the semipermeable membrane has a pore size configured to allow the blood-borne water in the vessel of the patient to permeate through the semipermeable membrane but not larger blood-borne metabolites including polypeptides or proteins, cell fragments, or cells.

5. The catheter according to claim 1, wherein the abluminal surface of the catheter includes a surface area-increasing means to increase a surface area of the abluminal surface over that without the surface area-increasing means, thereby increasing a flux of the blood-borne water from the vessel of the patient through the semipermeable membrane.

6. The catheter according to claim 1, wherein the influent is an aqueous solution including a dissolved polymer, and wherein the first osmotic concentration is sufficient to create an osmotic potential for removing blood-borne the water from the vessel in excess of that the patient needs through the semipermeable membrane.

7. A system for treating hypervolemia, comprising:

a) a catheter including:

a distal end portion having a closed distal end configured to at least temporarily reside within a vessel of a patient;

a luminal ingress joined to a luminal egress at the distal end portion, the luminal ingress designed to convey an influent having a first osmotic concentration to the distal end portion, wherein an abluminal surface of the luminal ingress is configured to be in direct contact with a fluid within the vessel of the patient; and a semipermeable membrane configured to pass blood-borne water from the vessel into at least the distal end portion, the blood-borne water absorbed by the influent to produce an effluent having a second osmotic concentration lower than the first osmotic concentration; and b) a fluid-collection system including:

a reservoir configured to collect the effluent; and a pump configured to move one or more fluids of the system including the influent and the effluent.

8. The system according to claim 7, the fluid-collection system further comprising an ultrafiltration membrane configured to produce a membrane permeate consisting essentially of the blood-borne water from the vessel of the patient and a membrane retentate for the influent.

9. The system according to claim 8, the fluid-collection system further comprising a shunt configured to shunt the membrane permeate to a bladder of the patient for elimination.

10. The system according to claim 8, the fluid-collection system further comprising a switch valve configured to switch a mode of the fluid-collection system from collecting the blood-borne water from the vessel of the patient in the reservoir to producing the membrane permeate and the membrane retentate for the influent.

11. The system according to claim 7, the catheter further comprising a septum disposed between the luminal ingress and the luminal egress, wherein a distal end of the septum is proximal of the closed distal end of the catheter.

12. The system according to claim 7, wherein the semipermeable membrane has a pore size configured to allow the blood-borne water in the vessel of the patient to permeate through the semipermeable membrane but not larger blood-borne metabolites including polypeptides or proteins, cell fragments, or cells.

13. The system according to claim 7, wherein the influent is an aqueous solution including a dissolved polymer, and wherein the first osmotic concentration is sufficient to create an osmotic potential for removing the blood-borne water from the vessel in excess of that the patient needs through the semipermeable membrane.

14. A method for treating hypervolemia, comprising:

inserting a closed-ended catheter in a vessel of a patient, the close-ended catheter comprising:

a distal end portion;

a luminal ingress joined to a luminal egress at the distal end portion; and a semipermeable membrane;

directing an influent into the luminal ingress having a first osmotic concentration;

absorbing blood-borne water from the vessel into at least the distal end portion through the semipermeable membrane to produce an effluent having a second osmotic concentration lower than the first osmotic concentration; and directing the effluent out of the closed-ended catheter by way of the luminal egress.

15. The method according to claim 14, further comprising: pumping the influent into the luminal ingress and pumping the effluent out of the luminal egress with a pump fluidly coupled to the closed-ended catheter.

16. The method according to claim 14, further comprising: disposing the effluent as a waste product.

17. The method according to claim 14, further comprising: recycling the effluent with a fluid-collection system to produce the influent.

18. The method according to claim 17, wherein directing the effluent out of the closed-ended catheter includes directing the effluent into a fluid reservoir of the fluid-collection system.

19. The method according to claim 18, further comprising: switching a mode of the fluid-collection system from collecting the effluent with the fluid reservoir to filtering the effluent with an ultrafiltration membrane of the fluid-collection system, wherein filtering the effluent produces a water-based membrane permeate and a membrane retentate of the influent.

20. The method according to claim 19, further comprising: shunting the water-based membrane permeate to a bladder of the patient for elimination.

21. The catheter according to claim 1, wherein the semipermeable membrane is disposed at the distal end portion.

22. The system according to claim 7, wherein the semipermeable membrane is disposed at the distal end portion.

23. The method according to claim 14, wherein the semipermeable membrane is disposed at the distal end portion.

* * * * *